United States Patent [19]
Park et al.

[11] Patent Number: 5,840,250
[45] Date of Patent: Nov. 24, 1998

[54] COMPOSITIONS AND METHODS FOR DISINFECTING A CONTACT LENS AND DETECTING THE PRESENCE OF AN OXIDATIVE DISINFECTANT

[75] Inventors: John Y. Park, Santa Ana; Lin Peng, Tustin; Anthony J. Dziabo, Lake Forest, all of Calif.

[73] Assignee: Allergan, Waco, Tex.

[21] Appl. No.: 938,493

[22] Filed: Sep. 30, 1997

Related U.S. Application Data

[62] Division of Ser. No. 496,867, Jun. 30, 1995, Pat. No. 5,703,024.

[51] Int. Cl.$^6$ .......................................................... A61L 2/18
[52] U.S. Cl. ................................. 422/28; 422/29; 422/30; 134/42; 510/100; 510/112; 510/113; 510/115; 510/373; 510/298
[58] Field of Search .................................. 422/28, 29, 30; 134/42; 510/100, 112, 113, 115, 298, 373; 252/408.1

[56] References Cited

U.S. PATENT DOCUMENTS

| | | |
|---|---|---|
| 3,183,173 | 5/1965 | Oakes . |
| 3,694,484 | 9/1972 | Factor et al. . |
| 3,910,296 | 10/1975 | Karageozian et al. . |
| 3,912,451 | 10/1975 | Gaglia . |
| 4,283,491 | 8/1981 | Dappen . |
| 4,295,851 | 10/1981 | Neumann et al. . |
| 4,521,375 | 6/1985 | Houlsby . |
| 4,568,517 | 2/1986 | Kaspar et al. . |
| 4,670,178 | 6/1987 | Huth et al. . |
| 4,851,353 | 7/1989 | Miike et al. . |
| 4,863,627 | 9/1989 | Davies et al. . |
| 5,079,140 | 1/1992 | Albarella . |
| 5,238,689 | 8/1993 | Dwyer . |
| 5,395,621 | 3/1995 | Amtower ................................ 424/613 |

FOREIGN PATENT DOCUMENTS 9211042  7/1992  WIPO .

OTHER PUBLICATIONS

Journal of American Chemical Society, 1989, vol. 111, No. 20 pp. 8030–8032.
Macromolecules 1987, vol. 20, No. 6, Alexandratos et al, pp. 1191–1196.
Journal of Polymer Science, Kamogawa et al, vol. 17, 3149–3157, 1979.
The Encyclopedia of Chemistry, 3RD ED., pp. 910–912, No Month available (1973).
The Encyclopedia of Chemistry, 3rd ED., pp. 852–854 No Month available (1973).
The Enzymes, vol. Xll, 3rd ED., pp. 557–567 No Month available (1975).

*Primary Examiner*—Margaret Einsmann
*Attorney, Agent, or Firm*—Frank J. Uxa

[57] ABSTRACT

Compositions and methods useful for disinfecting a contact lens are disclosed. The present methods comprise contacting a contact lens with a liquid medium containing an effective amount of an oxidative disinfectant component at conditions to effectively disinfect the contact lens. The contacting occurs in the presence of a color indicator component which is soluble in the liquid medium and is adapted to provide a color indication of the presence of the oxidative disinfectant component in the liquid medium. The color indicator component comprises an effective amount of a transition metal component which is redox active, has an oxidized state of a first color and a reduced state of a different second color and a polyanionic component in an amount effective to inhibit the staining of the contact lens by the transition metal component.

12 Claims, No Drawings

COMPOSITIONS AND METHODS FOR DISINFECTING A CONTACT LENS AND DETECTING THE PRESENCE OF AN OXIDATIVE DISINFECTANT

This is a continuation division of application Ser. No. 08/496,867 filed Jun. 30, 1995 now U.S. Pat. No. 5,703,052.

BACKGROUND OF THE INVENTION

The present invention relates to compositions and methods useful in disinfecting a contact lens. More particularly, this invention relates to such compositions and methods in which the presence of, and preferably the substantial absence of, an oxidative disinfectant is indicated.

Contact lenses should be periodically disinfected by the user to prevent infection or other deleterious effects on ocular health which may be associated with contact lens wear. Currently, there are several different conventional systems and methods which enable the user to disinfect his/her contact lenses between wearing times. These conventional cleaning and disinfection systems can be divided into "hot" and "cold" systems. Hot systems require the use of heat to disinfect the contact lenses, whereas cold systems use chemical disinfectants at ambient temperatures to disinfect the lenses.

Within the realm of cold disinfection systems are oxidative disinfectant, in particular hydrogen peroxide, disinfection systems. Disinfecting hydrogen peroxide solutions are effective to kill the bacteria and fungi which may contaminate contact lenses. However, residual hydrogen peroxide on a disinfected contact lens may cause irritation, burning or other trauma to the eye unless this hydrogen peroxide is destroyed, i.e., decomposed, neutralized, inactivated or chemically reduced. Therefore, destruction of the residual hydrogen peroxide in the liquid medium containing the disinfected contact lens is needed to enable safe and comfortable wear of the disinfected contact lens.

In order to avoid trauma to the eye caused by the presence of oxidative disinfectant on or in the lens, it would be advantageous to have an indication of the presence of such oxidative disinfectant. Additionally, it would be advantageous to have an indication of the substantial absence of such oxidative disinfectant, e.g., so that one would know it was safe to place the disinfected lens into one's eye.

A number of soluble color indicators have been suggested for use in contact lens disinfecting service. See, for example, Huth et al U.S. Pat. No. 4,670,178 and Davies et al U.S. Pat. No. 4,863,627. The use of soluble color indicators has certain disadvantages. For example, the soluble color indicator comes into intimate contact with the contact lens being treated and may have a detrimental effect on the lens and/or on the wearer of the lens.

Insoluble color indicators, such as those described in Amtower U.S. Pat. No. 5,362,444 and 5,395,621 are effective and advantageously keep the contact lens separated from the active color indicator. One disadvantage of such insoluble indicators is that the response time to a change in the concentration of oxidative disinfectant is relatively slow, which can result in unnecessary delays in placing disinfected lenses in the wearer's eyes or even placing active disinfectant in the lens wearer's eyes.

Color indication or indications of the presence and absence of hydrogen peroxide should be clear and distinct and should be provided in a timely manner. Also, the color indicator component should be selected so that the lens and the lens wearer are not adversely affected.

There continues to be a need for a contact lens care system which effectively disinfects a contact lens and provides an indication of the presence of the oxidative disinfectant so that the disinfected lens can be safely and comfortably worn.

SUMMARY OF THE INVENTION

New compositions and methods for disinfecting, and preferably cleaning, contact lenses have been discovered. The present systems provide clear, positive and timely indications of the presence, and preferably of the absence, of an oxidative disinfectant, preferably hydrogen peroxide, in the lens disinfecting medium. The indication of the presence of an oxidative disinfectant warns the lens wearer not to place the lens directly from the oxidative disinfectant-containing medium into the eye. Importantly, the color indications are given in a timely manner. The present color indicator components are safe, preferably are useful when peroxidases, such as catalase, alone are used to destroy residual oxidative disinfectant, do not interfere with the disinfecting method and have no substantial detrimental effect on the lens being disinfected or on the wearer of the disinfected contact lens. The present invention takes advantage of the use of soluble color indicator components and color differences in transition metal components to provide the indication or indications noted herein. Such color differences are particularly timely, clear and distinct, which greatly adds to the usefulness of the present system. Moreover, the present invention effectively provides for the use of transition metal components so that concerns regarding potential toxicity to the eye and contact lens coloring or staining are substantially reduced, or even eliminated.

In one broad aspect, the present invention is directed to compositions useful in disinfecting a contact lens. Such compositions comprise a liquid medium, an oxidative disinfectant component and a color indicator component. The oxidative disinfectant component, preferably hydrogen peroxide, is present in an amount effective to disinfectant a contact lens immersed in the composition. The color indicator component is soluble in the liquid medium and is adapted and effective to provide a color indication of the presence of the oxidative disinfectant component in the liquid medium. The color indicator component comprises an effective amount of a transition metal component which is redox active, has an oxidized state of a first color and a reduced state of a different second color and a polyanionic component present in an amount effective to inhibit the staining of a contact lens immersed in the composition by the transition metal component. Preferably, the transition metal component in the oxidized state is effective to provide the color indication of the presence of the oxidative disinfectant component in the liquid medium.

In a particularly useful embodiment, the polyanionic component is selected from polymeric materials having multiple anionic charges and mixtures thereof. A particularly useful transition metal component is ruthenium red.

In another broad aspect of the present invention, compositions are provided which comprise at least one solid item including a color indicator component. This color indicator component which is soluble in a liquid aqueous medium, is adapted to provide a color indication of the presence, and preferably the absence, of an oxidative disinfectant component in a liquid aqueous medium in which the composition is placed. The color indicator component comprises a transition metal component which is redox active, has an oxidized state of a first color and a reduced state of a different second color in an amount effective to provide a color indication of the presence of an oxidative disinfectant component in a liquid aqueous medium, and a polyanionic component in an amount effective to inhibit the staining of a contact lens immersed in a liquid aqueous medium containing the color indicator component in a solubilized form by the transition metal component. In a particularly useful embodiment, the solid item includes at least one of an effective amount of a contact lens cleaning enzyme component and an effective amount of an oxidative disinfectant destroying component. Preferably, the composition is structured to release the color indicator component in a liquid aqueous medium prior to releasing the oxidative disinfectant destroying component.

In a further broad aspect of the present invention, methods for disinfecting a contact lens are provided. This method comprises contacting a contact lens with a liquid medium containing an effective amount of an oxidative disinfectant component at conditions to effectively disinfect a contact lens. This contacting occurs in the presence of a color indicator component which is soluble in the liquid medium. The color indicator component is adapted to provide a color indication of the presence, and preferably the absence, of the oxidative disinfectant component in the liquid medium. The color indicator component comprises an effective amount of a transition metal component which is redox active, has an oxidized state of a first color and a reduced color of a different second color and a polyanionic component in an amount effective to inhibit the staining of the contact lens by the transition metal component.

These and other aspects of the present invention are apparent in the following detailed description of the invention, examples and claims.

DETAILED DESCRIPTION OF THE INVENTION

The present invention is of value where oxidative disinfectants, in particularly hydrogen peroxide, are used to disinfect all types of lenses, e.g., contact lenses, which are benefitted by periodical disinfecting. Such lenses, e.g., conventional contact lenses, and preferably soft contact lenses, may be made of any suitable material or combination of materials and may have any suitable configuration not substantially deleteriously affected by such oxidative disinfectants.

Although any oxidative disinfectant component which is able to effectively disinfect a contact lens may be employed in accordance with the present invention, the much preferred oxidative disinfectant is hydrogen peroxide, especially aqueous solutions including hydrogen peroxide.

The color indicator component includes a transition metal component and a polyanionic component. The transition metal component is redox active, has an oxidized state of a first color and a reduced state of a different second color.

As used herein, the term "redox active" means that the component or material in question is capable of being oxidized from a reduced state to an oxidized state at the conditions present in a liquid aqueous medium containing oxidative disinfectant component, and is capable of being reduced from the oxidized state to the reduced state at the conditions present in the same liquid aqueous medium which is substantially free of oxidative disinfectant component. Thus, the presently useful transition metal components are present in an oxidized state in an oxidative disinfectant component-containing liquid aqueous medium. After all the oxidative contact lens disinfectant component in this liquid aqueous medium has been destroyed, for example, chemically reduced or decomposed, the transition metal component is present in the liquid aqueous medium in a reduced state.

Any transition metal component having the characteristics identified herein and suitable for functioning as part of the present color indicator component may be employed in accordance with the present invention. The transition metal component preferably comprises a metal selected from ruthenium, other platinum group metals, cobalt, copper, chromium and the like and mixtures thereof. The transition metal component may be incorporated into the present color indicator component in any suitable form provided that such transition metal component functions as described herein. Ruthenium red is a particularly useful transition metal component.

The amount of transition metal component is sufficient to provide the desired color indication or indications. For example, the transition metal component can be present in an amount in the range of about 0.0001% by weight or less to about 1% or 2% by weight or more, based on the weight of the liquid medium employed. Excessive amounts of transition metal components should be avoided as being wasteful and because such amounts may have detrimental effects on the contact lens and/or the wearer of the contact lens.

Any suitable polyanionic component may be employed in accordance with the present invention provided that it functions as described herein and has no substantial detrimental effect on the contact lens being disinfected or on the wearer of the disinfected contact lens. The polyanionic component is preferably ophthalmically acceptable at the concentrations used to inhibit staining of the contact lenses. The polyanionic component preferably includes three (3) or more anionic (or negative) charges. In the event that the polyanionic component is a polymeric material, it is preferred that each of the repeating units of the polymeric material include a discrete anionic charge. Particularly useful anionic components are those which are water soluble, for example, soluble at the concentrations used in the presently useful liquid aqueous media, such as a liquid aqueous medium containing the polyanionic component, the transition metal component and the oxidative disinfectant component.

In one embodiment, the polyanionic component is sufficiently anionic to be effective to form one or more complexes with the transition metal component in a liquid medium, for example, a liquid aqueous medium.

A particularly useful class of polyanionic components are one or more polymeric materials having multiple anionic charges. Examples include:

metal carboxymethylcelluloses
    metal carboxymethylhydroxyethylcelluloses
    metal carboxymethylstarchs
    metal carboxymethylhydroxyethylstarchs
    hydrolyzed polyacrylamides and polyacrylonitriles
    heparin
    homopolymers and copolymers of one or more of:
        acrylic and methacrylic acids
        metal acrylates and methacrylates
        alginic acid
        metal alginates
        vinylsulfonic acid
        metal vinylsulfonate
        amino acids, such as aspartic acid, glutamic acid and the like
        metal salts of amino acids p-styrenesulfonic acid
metal p-styrenesulfonate
2-methacryloyloxyethylsulfonic acids
metal 2-methacryloyloxethylsulfonates
3-methacryloyloxy-2-hydroxypropylsulfonic acids
metal 3-methacryloyloxy-2-hydroxypropylsulfonates
2-acrylamido-2-methylpropanesulfonic acids
metal 2-acrylamido-2-methylpropanesulfonates
allylsulfonic acid
metal allylsulfonate and the like.

The present polyanionic components often can exist in the un-ionized state, for example, in the solid state, in combination with a companion or counter ion, in particular a plurality of discrete cations equal in number to the number of discrete anionic charges so that the un-ionized polyanionic component is electrically neutral. For example, the present un-ionized polyanionic components may be present in the acid form and/or in combination with one or more metals. Since the polyanionic components are preferably ophthalmically acceptable, it is preferred that the metal associated with the un-ionized polyanionic component be ophthalmically acceptable in the concentrations used. Particularly useful metals include the alkali metals, for example, sodium and potassium, the alkaline earth metals, for example, calcium and magnesium, and mixtures thereof. Sodium is very useful to provide the counter ion in the un-ionized polyanionic component. Polyanionic components which, in the un-ionized states, are combined with cations other than $H^+$ and metal cations can be employed in the present invention.

Particularly useful polyanionic components are selected from anionic cellulose derivatives, anionic polymers derived from acrylic acid (meaning to include polymers from acrylic acid, acrylates and the like and mixtures thereof), anionic polymers derived from aspartic acid, anionic polymers derived from methacrylic acid (meaning to include polymers from methacrylic acid, methacrylates, and the like and mixtures thereof), anionic polymers derived from alginic acid (meaning to include alginic acid, alginates, and the like and mixtures thereof), anionic polymers derived from amino acids (meaning to include amino acids, amino acid salts, and the like and mixtures thereof) and mixtures thereof. Very useful polyanionic components are those selected from anionic polymers derived from aspartic acid, and mixtures thereof.

The amount of polyanionic component employed is that effective to inhibit the staining of a contact lens by the transition metal component, as described herein. The specific amount of such component used is not critical to the present invention provided that it functions as a staining inhibitor, as described herein. In addition, the amount of polyanionic component employed depends on a number of factors, for example, the specific polyanionic component being employed, the specific transition metal component being employed and the specific transition metal component concentration being employed. In addition, excessive amounts of polyanionic component are preferably to be avoided since this may be wasteful and unnecessary and may have an adverse impact on the wearer of the disinfected contact lens. Preferably, the polyanionic component is present in an amount of at least about 0.001% or at least about 0.005% to about 5% or about 2% or about 1%, based on the weight of the liquid disinfecting medium.

In a particularly useful embodiment, the weight ratio of polyanionic component to transition metal component in the present color indicator components is preferably at least about 2, and more preferably in the range of about 4 to about 10 or about 20 or more.

Without wishing to limit the invention to any particular theory of operation, it is believed that the ratio of polyanionic component to transition metal component is important in order that the polyanionic component be present in an amount effective to form water soluble complexes with the transition metal component such that the transition metal component, in the complexed state, has a reduced propensity to stain the contact lens. In other words, it is believed that the present polyanionic component is preferably included in the present compositions in amounts effective to form complexes which effectively inhibit the transition metal component from staining the contact lens present in the contact with the liquid aqueous medium.

In one embodiment, the present polyanionic components are combined with the transition metal components in one or more solid particles, for example, prior to use. To illustrate, a mixture containing a polyanionic component and the transition metal component can be formed into a suitably sized and configured pill or tablet, for example, using conventional techniques. When it is desired to disinfect a contact lens, the lens is placed into an oxidative disinfectant-containing liquid medium, for example, a hydrogen peroxide-containing liquid aqueous medium, together with the pill or tablet, which dissolves into the liquid medium. The contact lens is disinfected. In addition, the polyanionic component is effective to inhibit staining of the contact lens by the transition metal component before, during and after disinfection. After the disinfectant component is effectively destroyed, the disinfected lens can be removed from the liquid medium and placed directly in the eye for safe and comfortable wear. Alternately, the disinfected lens can be removed from the liquid medium, rinsed free of the liquid medium, for example, using a buffered saline, and then placed in the eye for safe and comfortable wear. The combination of transition metal component and polyanionic component effectively provides timely indications of the presence and absence of oxidative disinfectant component, without detrimentally affecting, e.g., staining the lens.

The liquid medium used in disinfecting a contact lens in the present invention preferably includes a disinfecting amount of oxidative disinfectant, preferably hydrogen peroxide. Preferably, a disinfecting amount of oxidative disinfectant means such amount as will reduce the microbial burden by one log in three hours. Still more preferably, the hydrogen peroxide concentration is such that the microbial load is reduced by one log order in one hour. Particularly preferred are those hydrogen peroxide concentrations which reduce the microbial load by one log unit in 10 minutes or less. Aqueous hydrogen peroxide solutions, preferably containing about 0.2% or about 0.5% to about 5% or about 6% of hydrogen peroxide (w/v), are known to be effective disinfecting solutions for contact lenses. These solutions are effective at killing bacteria and fungi which may be found on contact lenses. Typically, the amount of hydrogen peroxide used in the liquid medium is well in excess of that required to effectively disinfect a contact lens. Substantial excess hydrogen peroxide is used so that the lens disinfection can be completed in a reasonable period of time.

The liquid medium used is selected to have no substantial detrimental effect on the lens being treated and to allow, and preferably to even facilitate, the present lens treatment or treatments. The liquid medium is preferably aqueous-based. A particularly useful liquid aqueous medium is that derived from saline, e.g., a conventional saline solution. During the disinfecting contacting, it is preferred that the liquid aqueous medium have a pH in the range of about 3 to about 9, more preferably about 6 to about 8. The liquid medium, e.g., aqueous liquid medium, preferably includes a buffer which is present in an amount effective to maintain the pH of the liquid medium in the desired range. This buffer may be present in the liquid medium and/or may be introduced into the liquid medium. Among the suitable buffers or buffering agents which may be employed are those which are conventionally used in contact lens care products. Examples of useful buffers include those with carbonate functionalities, bicarbonate functionalities, phosphate functionalities, borate functionalities, and the like and mixtures thereof. The buffers may be alkali metal and alkaline earth metal salts, in particularly sodium and potassium.

In one embodiment, an oxidative disinfectant destroying component, hereinafter referred to as an ODDC, is included in a solid composition, e.g., a tablet, capsule, one or more solid particles and the like, which is preferably introduced into the liquid medium about the same time as the lens to be disinfected is introduced into the liquid medium. Such solid compositions include one or more ODDCs in an amount effective to destroy all the residual oxidative disinfectant remaining in the liquid medium after the lens has been disinfected and preferably to reduce the polymer matrix material and the transition metal component of the color indicator component to the reduced states.

Thus, such preferred solid compositions, which are preferably initially contacted with the oxidative disinfectant-containing liquid medium at substantially the same time as is the lens to be disinfected, allow for effective lens disinfection and, in addition, effectively destroy the residual oxidative disinfectant remaining in the oxidative disinfectant-containing liquid medium so that the disinfected lens can be removed from the liquid medium and placed directly into the eye for safe and comfortable wear. If, as is preferred, the transition metal component of the color indicator component is also reduced and a second color indication of the substantial absence of the oxidative disinfectant is provided while the contact lens remains in the liquid medium, thus giving added assurance to the lens wearer that it is safe to remove the lens from the liquid medium and to wear the disinfected lens. Such preferred compositions may be present in the form of at least one item, e.g., tablet, capsule, one or more solid particles and the like, which includes a coated portion, e.g., a core such as a core tablet, and a barrier component. The coated portion includes the ODDC or ODDCs from the coated portion into the liquid medium for a period of time, preferably sufficient to allow the lens to be disinfected. Preferably, the barrier coating substantially surrounds the coated portion.

Any suitable ODDC may be employed provided such ODDC has no substantial detrimental effect on the present system, on the disinfected lens or on the wearer of the disinfected lens. Among the useful ODDCs are oxidative disinfectant reducing agents, peroxidases (meaning to include therein catalase) and mixtures thereof.

Examples of the oxidative disinfectant reducing agents which are useful in the present invention are alkali metal, in particular sodium, thiosulfates; thiourea; alkali metal, in particular sodium, formates; pyruvic acid and salts of pyruvic acid; N-acetylcysteine; ene-diol compounds, e.g., ascorbic acid compounds, reductive acid compounds, isoascorbic acid compounds, glyoxylic acid compounds, squaric acid compounds, dihydroxymaleic acid compounds, dihydroxyfumaric acid compounds; and mixtures thereof. Typical examples of the foregoing ene-diol compounds are the acids themselves, e.g., ascorbic acid, ophthalmically acceptable salts of such acids, e.g., sodium ascorbate, ophthalmically acceptable esters of such acids, e.g., ascorbic palmitate and any other ophthalmically acceptable derivatives of such acids, e.g., that retain the ene-diol molecular structure, mixtures thereof and the like. A particularly useful peroxidase is catalase. The peroxidases, and especially catalase, are very beneficial in the present invention since such ODDCs are effective to substantially eliminate hydrogen peroxide from a liquid medium in a reasonable period of time, e.g., on the order of about 1 minute to about 12 hours, preferably about 5 minutes to about 1 hour, after being initially released into the liquid medium.

The amount of ODDC employed is preferably sufficient to destroy all the oxidative disinfectant present in the liquid medium into which the ODDC is placed. Excess ODDC may be employed. Very large excesses of ODDC are to be avoided since the ODDC itself may cause problems with the disinfected lens and/or the ability to safely and comfortably wear such disinfected lens. When catalase is employed as all or a part of the ODDC, it is preferably present in an amount of about 100 to about 1000, more preferably about 150 to about 700 units of catalase activity per milliliter of liquid medium. For example, an especially useful amount of catalase for use in an aqueous solution containing about 3% (w/v) hydrogen peroxide is about 520 units of catalase activity/ml of solution.

The delayed release of the ODDC into the liquid medium may be accomplished in any one of many suitable ways, a number of which are conventional and well known in the art. For example, a delayed release or barrier component, e.g., coating, may be provided by coating a core tablet, or other particles, containing the ODDC with a slow dissolving coating material, which may ultimately be completely or only partially soluble in the liquid medium, or by including the ODDC in a matrix from which it may be slowly leached. Also, the matrix may be coated with a slow dissolving material so that the start of the slow release is delayed. The delayed release form of the ODDC is preferably such that substantially no release occurs during a delay period followed by rapid and substantially complete release of the ODDC at the end of the delay period. Such a result may be obtained by coating the ODDC with a slow dissolving coating.

Although multi-layered (including core and one or more coating layers) tablets or pills are preferred, the delayed release form of the present compositions can be present in any other suitable item or items, such as masses of powders, granules and the like. Delayed release technology is well known in the art as exemplified by the text *Controlled Drug Delivery*, 2nd Ed., Joseph R. Robinson & Vincent H. L. Lee, Eds., Marcel Dekker, Inc., N.Y., 1987.

Any suitable delayed release component or combination of delayed release components may be employed, provided that such component or components function as described herein and have no substantially detrimental effect on the other components present, on the lens being treated and on the human wearing the treated lens. The delayed release component is preferably at least partially, more preferably completely, water soluble. The delayed release component preferably comprises a major amount of at least one polymeric material.

Delayed release or barrier components suitable as either coatings or as matrices, include water soluble vinyl polymers, such as polyvinylpyrrolidone, polyvinylalcohol and polyethyleneglycol; water soluble proteins; polysaccharide and cellulose derivatives, such as methyl cellulose and hydroxypropylmethyl cellulose; and the like and mixtures thereof.

The amount of delayed release or barrier component used is not critical in the present invention provided that such component functions as described herein. The delayed release or barrier component may suitably be present in the range of about 1% to about 20% or more, based on the weight of the ODDC.

The solid compositions may be produced using any one of many suitable methods, a number of which are conventional and well known in the art.

The solid compositions may include other components, for example, fillers, binders, tonicity agents, contact lens conditioning/wetting agents, buffering agents, lubricating agents and the like. Each of these components may be present, if at all, in an amount effective to perform its designated function or functions. Examples of each of these types of components are conventional and well known in the art. Therefore, a detailed description of such components is not presented here.

In a particularly useful embodiment, the contact lens may be subjected to the action of at least one enzyme effective to remove debris from a contact lens. Among the types of debris that form on contact lens during normal use are protein-based debris, mucin-based debris, lipid-based debris and carbohydrate-based debris. One or more types of debris may be present on a single contact lens.

The enzyme employed may be selected from peroxide-active enzymes which are conventionally employed in the enzymatic cleaning of contact lenses. For example, many of the enzymes disclosed in Huth et al U.S. Pat. No. 4,670,178 are useful in the present invention. The disclosure of this patent is incorporated in its entirety by reference herein. Among the useful enzymes are those selected from proteolytic enzymes, lipases and mixtures thereof.

Preferred proteolytic enzymes are those which are substantially free of sulfhydryl groups or disulfide bonds, whose presence may react with the active oxygen of the disinfectant to the detriment of the activity of the enzymes. Metalloproteases, those enzymes which contain a divalent metal ion such as calcium, magnesium or zinc bound to the protein, may also be used.

A more preferred group of proteolytic enzymes are the serine proteases, particularly those derived from Bacillus and Streptomyces bacterial and Aspergillus molds. Within this grouping, the still more preferred enzymes are the derived alkaline proteases generically called subtilisin enzymes. Reference is made to Deayl, L., Moser, P. W. and Wildi, B. S., "Proteases of the Genus Bacillus. II Alkaline Proteases", Biotechnology and Bioengineering, Vol. XII, pp. 213–249 (1970) and Deayl, L. and Moser, P. W., "Differentiation of Alkaline Proteases Form Bacillus Species" Biochemical and Biophysical Research Comm., Vol. 34, No. 5, pp. 600–604 (1969).

The subtilisin enzymes are broken down into two subclasses, subtilisin A and subtilisin B. In the subtilisin A grouping are enzymes derived from such species as *B. subtilis, B. licheniformis* and *B. pumilis*. Organisms in this sub-class produce little or no neutral protease or amylase. The subtilisin B sub-class is made up of enzymes from such organisms as *B. subtilis, B. subtilis var. amylosacchariticus, B. amyloliquefaciens* and *B. subtilis* NRRL B3411. These organisms produce neutral proteases and amylases on a level about comparable to their alkaline protease production. One or more enzymes from the subtilisin A sub-class are particularly useful.

In addition, other preferred enzymes are, for example, pancreatin, trypsin, collagenase, keratinase, carboxylase, aminopeptidase, elastase, and aspergillo-peptidase A and B, pronase E (from *S. griseus*) and dispase (from *Bacillus polymysxa*).

If such an enzyme or enzymes are employed, an effective amount is preferably used. Such amount will be that amount which effects removal in a reasonable time (for example overnight) of substantially all of at least one type of debris from a lens due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective cleaner will depend on several factors, including the inherent activity of the enzyme, and the extent of its interaction with the hydrogen peroxide present.

As a basic yardstick, the working solution should contain sufficient enzyme to provide about 0.001 to about 3 Anson units of activity, preferably about 0.01 to about 1 Anson units of activity, preferably about 0.01 to about 1 Anson units, per single lens treatment. Higher or lower amounts may be used.

Enzyme activity is pH dependent so for any given enzyme, there is a particular pH range in which that enzyme will function best. The determination of such range can readily be done by known techniques.

Solid compositions which include such lens cleaning enzymes may be structured to release the enzyme, into the liquid medium which contacts the composition, at any time relative to the other component or components of the composition provided that the released enzyme is effective at the conditions present in the liquid medium to perform the cleaning function, as described herein. In one particularly useful embodiment, the cleaning enzyme is released into the liquid medium substantially immediately upon introducing the solid composition into the liquid medium.

In the event that a debris removing enzyme is present, the contact lens in the liquid medium is effectively cleaned of such debris. This cleaning action can occur before the lens is disinfected, at the time the lens is being disinfected, or after the lens is disinfected.

The disinfecting contacting preferably occurs at a temperature to maintain the liquid medium substantially liquid. It is preferred that the contacting temperature be in the range of about 0° C. to about 100° C., and more preferably in the range of about 10° C. to about 60° and still more preferably in the range of about 15° C. to about 30° C. Contacting at or about ambient temperature is very convenient and useful. The contacting preferably occurs for a time to substantially completely disinfect the lens being treated. Such contacting times can be in the range of about 1 minute to about 12 hours or more.

After such contacting, the liquid medium preferably includes substantially no residual, oxidative disinfectant and the disinfected lens can be removed from this liquid medium and placed directly into the eye for safe and comfortable wear. However, if the liquid medium includes one or more "cleaning" enzymes, it is preferred to rinse the disinfected lens, e.g., with saline, to free the lens of such enzyme prior to placing the disinfected lens into the eye.

The following non-limiting examples illustrate certain aspects of the present invention.

EXAMPLE 1

Aqueous hydrogen peroxide solutions were added to a combination of ruthenium red (10 ppm by weight of the solution) and poly(aspartic acid) (100 ppm by weight of the solution). Color changes of these solutions are summarized in the following table:

| H$_2$O$_2$ | COLORS/COLOR CHANGE | TIME TO CHANGE |
|---|---|---|
| 0.3% (w/v) | pink to yellow | instantaneously |
| 0.03% (w/v) | pink to yellow | instantaneously |
| 0.003% (w/v) | pink to yellow | 5 minutes |
| 0.0003% (w/v) | pink | did not change |

These results demonstrate that the response time of the color indicators (soluble ruthenium red) was very rapid and effectively indicated the presence of hydrogen peroxide above 0.0003% (w/v) concentration.

EXAMPLE 2

Contact lenses, made of an ionic, high water content hydrogel material, were soaked in phosphate buffered saline (pH 7.4) containing 10 ppm by weight of the solution of ruthenium red and ethylenediaminetetraacetic acid or citric acid at various concentrations. All lenses were stained by ruthenium red within one hour. When the same test was attempted with sodium hexametaphosphate, the ruthenium red was decomposed and no staining experiment could be done.

EXAMPLE 3

Contact lenses, made of an ionic, high water content hydrogel material, were soaked in phosphate buffered saline (pH 7.4) containing 20 ppm by weight of the solution of ruthenium red and poly(acrylic acid) (PAA) at various concentrations. Staining on the lenses were checked periodically and results are summarized in the following table:

| Poly(Acrylic Acid), ppm by weight of solution | TIME, hours | LENS COLOR |
|---|---|---|
| 0 | 3 | pink |
| 50 | 3 | clear |
| 50 | 6 | clear |
| 100 | 3 | clear |
| 100 | 6 | clear |

The solutions of ruthenium red and poly(acrylic acid) lost their pink color in a couple of days and no long term observations on the staining of lenses were made.

EXAMPLE 4

Contact lens, made of an ionic, high water content hydrogel material, were soaked in phosphate buffered saline (pH 7.2) containing 8 ppm by weight of the solution of ruthenium red and poly(aspartic acid) (PASP) at various concentrations. Staining of lenses by ruthenium red was checked periodically and the results are summarized in the following table:

| (Poly Aspartic Acid), ppm by weight of solution | TIME, hours | Lens Color |
|---|---|---|
| 0 | 2 hours | pink |
| 40 ppm | 2 hours | pink |
| 80 ppm | 2, 8 and 24 hrs. | clear |
| 100 ppm | 2, 8 and 24 hrs. | clear |
| 120 ppm | 2, 8 and 24 hrs. | clear |

EXAMPLE 5

This experiment was a continuation of Example 4. Similar lenses in the buffered saline were kept in the dark (ruthenium red is light sensitive) at room temperature for the long term observation. The saline containing ruthenium red and poly (aspartic acid) maintained the pink color for four months. The lenses were checked for staining periodically and the results are summarized in the following table:

| (Poly Aspartic Acid), ppm by weight of solution | TIME, days | Lens Color |
|---|---|---|
| 0 | 30, 60 and 120 | pink |
| 80 ppm | 30, 60 and 120 | clear |
| 100 ppm | 30, 60 and 120 | clear |
| 120 ppm | 30, 60 and 120 | clear |

EXAMPLE 6

A contact lens, made of a nonionic, high water content hydrogel material, was soaked in phosphate buffered saline containing 4 ppm by weight of the solution of ruthenium red and 40 ppm by weight of the solution of poly(aspartic acid). A second, similar contact lens was soaked in a similar buffered saline containing 4 ppm by weight of the solution of ruthenium red and 80 ppm by weight of the solution of poly(aspartic acid). Both lenses remained clear even after four months in the dark at room temperature while the solutions maintained their pink color.

EXAMPLE 7

A pair of protein-based debris laden contact lenses are placed in a conventional lens vial. 10 ml of a saline solution containing 3% (w/v) of H$_2$O$_2$, 0.3% by weight of boric acid, 10 ppm by weight of the solution of ruthenium red and 100 ppm by weight of the solution of poly(aspartic acid) is added to the vial so that the contact lenses are completely submerged in the solution. The pH of this solution is about 7.5. At this point the solution is yellow in color.

A layered, delayed release tablet is dropped into the solution in the lens vial. The center core of the tablet includes 2.0 mg of crystalline catalase. The outer layer of the tablet includes 0.4 mg of subtilisin A enzyme. A delayed release layer between the inner layer and the outer layer is structured and designed to dissolve sufficiently in two hours after being exposed to the solution in the lens vial to release the catalase into the solution.

Upon being dropped into the solution, the outer layer of the tablet dissolves to release the subtilisin A into the solution. The enzyme in the outer layer begins to attack and remove the protein-based debris on the lenses. Substantially all of the protein-based debris is removed from the lenses. In addition, the contact lenses are effectively disinfected. Two hours after the layered tablet is first dropped into the solution, the catalase is released into the solution and destroys the residual hydrogen peroxide in the solution and the ruthenium red is reduced to a reduced state. The solution turns pink in color.

Upon seeing the pink solution, the lens wearer removes the cleaned/disinfected lenses from the solution, rinses them with physiological saline solution to remove the subtilisin A enzyme, and places them in his/her eyes. It is found that the contact lenses are effectively disinfected and cleaned of protein-based debris. The lens wearer experiences no discomfort or eye irritation from wearing the disinfected and cleaned contact lenses.

EXAMPLE 8

A pair of protein-based debris laden contact lenses are placed in a conventional lens vial. 10 ml of a saline solution containing 3% (w/v) of $H_2O_2$ and 0.3% by weight of boric acid is added to the vial so that the contact lenses are completely submerged in the solution. The pH of this solution is about 7.5.

A layered, delayed release tablet is dropped into the solution in the lens vial. The center core of the tablet includes 2.0 mg of crystalline catalase. The outer layer of the tablet includes 0.4 mg of subtilisin A enzyme, 0.1 mg of ruthenium red and 1.0 mg of poly(aspartic acid). A delayed release layer between the inner layer and the outer layer is structured and designed to dissolve sufficiently in two hours after being exposed to the solution in the lens vial to release the catalase into the solution.

Upon being dropped into the solution, the outer layer of the tablet dissolves to release the subtilisin A into the solution. At this point, the solution is yellow in color. The enzyme in the outer layer begins to attack and remove the protein-based debris on the lenses. Substantially all of the protein-based debris is removed from the lenses. In addition, the contact lenses are effectively disinfected. Two hours after the layered tablet is first dropped into the solution, the catalase is released into the solution and destroys the residual hydrogen peroxide in the solution and the ruthenium red is reduced to a reduced state. The solution turns pink in color. Upon seeing the pink solution, the lens wearer removes the cleaned-disinfected lenses from the solution, rinses them with physiological saline solution to remove the subtilisin A enzyme, and places them in his/her eyes. It is found that the contact lenses are effectively disinfected and cleaned of protein-based debris. The lens wearer experiences no discomfort or eye irritation from wearing the disinfected and cleaned contact lenses.

While this invention has been described with respect to various specific examples and embodiments, it is to be understood that the invention is not limited thereto and that it can be variously practiced within the scope of the following claims.

What is claimed is:

1. A method for disinfecting a contact lens comprising:
    contacting a contact lens with an aqueous liquid medium containing an effective amount of an oxidative disinfectant component at conditions to effectively disinfect and contact lens, said contacting occurring in the presence of a color indicator component which is soluble in said liquid medium and is adapted to provide a color indication of the presence of said oxidative disinfectant component in said liquid medium, said color indicator component comprising an effective amount of a transition metal component which is redox active, has an oxidized state of a first color and a reduced state of a different second color and a polymeric polyanionic component in an amount effective to inhibit the staining of said contact lens by said transition metal component.

2. The method of claim 1 which further comprises destroying said oxidative disinfectant component so as to provide a substantially oxidative disinfectant-free liquid medium, said transition metal component being reduced to said reduced state which provides a different color indication of the substantial absence of said oxidative disinfectant component in said liquid medium.

3. The method of claim 2 wherein a peroxidase component is present during said destroying step in an amount effective to provide said substantially oxidative disinfectant-free liquid medium.

4. The method of claim 1 wherein said polymeric polyanionic component is selected from the group consisting of polymeric material having multiple anionic charges and mixtures thereof.

5. The method of claim 1 wherein said polymeric polyanionic component is selected from the group consisting of anionic cellulose derivatives, anionic polymers derived from acrylic acid, anionic polymers derived from aspartic acid, anionic polymers derived from glutamic acid, anionic polymers derived from alginic acid, anionic dextran derivatives and mixtures thereof.

6. The method of claim 1 wherein in said aqueous medium liquid medium, said oxidative disinfectant component is hydrogen peroxide, said transition metal component is ruthenium red and said polymeric component is selected from the group consisting of anionic polymers derived from aspartic acid and mixtures thereof.

7. The method of claim 1 wherein said polymeric polyanionic component is effective to form one or more complexes with said transition metal component in said liquid medium.

8. The method of claim 1 which further comprises contacting said contact lens with an enzyme component capable of removing deposit material from a contact lens in an amount effective to remove deposit material from said contact lens.

9. A method for disinfecting a contact lens comprising:
    providing a solid item in the form of a pill or tablet comprising a color indicator component;
    contacting an aqueous contact lens with a liquid medium containing an effective amount of an oxidative disinfectant component at conditions to effectively disinfect said contact lens, said contacting occurring in the presence of at least one of said solid item comprising said color indicator component, said component being soluble in said liquid medium and, in a solubilized form, is adapted to provide a color indication of the presence of said oxidative disinfectant component in said liquid medium, said color indicator component comprising a transition metal component which is redox active, has an oxidized state of a first color and a reduced state of a different second color in an amount effective to provide the color indication of the presence of said oxidative disinfectant component in said aqueous liquid medium, and a polymeric polyanionic component in an amount effective to inhibit the staining of said contact lens by said transition metal component in a solubilized form.

10. The method of claim 9 wherein said at least one solid item further includes an effective amount of a contact lens cleaning enzyme component.

11. The method of claim 9 wherein said at least one solid item further includes an effective amount of an oxidative disinfectant destroying component.

12. The method of claim 11 which said solid item is structured to release said color indicator component in a liquid aqueous medium prior to said oxidative disinfectant destroying component.

* * * * *